United States Patent [19]

Harwell

[11] Patent Number: 5,505,616
[45] Date of Patent: Apr. 9, 1996

[54] DISTALIZING SPRING

[76] Inventor: Anthony L. Harwell, 3420 Thornton, Amarillo, Tex. 79109

[21] Appl. No.: 68,812

[22] Filed: May 27, 1993

[51] Int. Cl.[6] .................................................. A61C 3/00
[52] U.S. Cl. ............................................ 433/21; 433/24
[58] Field of Search ................................. 433/7, 18, 19, 433/21, 22, 24

[56] References Cited

U.S. PATENT DOCUMENTS

| | | | |
|---|---|---|---|
| 2,580,042 | 12/1951 | Paus | 433/21 |
| 3,293,747 | 12/1966 | Denholtz | 433/21 |
| 3,936,938 | 2/1976 | Northcutt | 433/21 |
| 3,997,970 | 12/1976 | Hodgson | 433/19 |
| 4,255,139 | 3/1981 | Ladanyi | 433/21 |
| 4,571,178 | 2/1986 | Rosenberg | 433/19 X |
| 5,011,404 | 4/1991 | Losi | 433/21 X |
| 5,022,855 | 6/1991 | Jeckel | 433/18 |
| 5,064,370 | 11/1991 | Jones | 433/21 |
| 5,120,218 | 6/1992 | Hanson | 433/19 |
| 5,167,500 | 12/1992 | Miura | 433/7 |
| 5,299,935 | 4/1994 | Lokar | 433/18 |

*Primary Examiner*—Nicholas D. Lucchesi
*Attorney, Agent, or Firm*—Kenyon & Kenyon

[57] ABSTRACT

A device for distalizing maxillary molars. The device comprises a spring attached to a tubular head and an attached ligature tie wire. The device is attached by a ligature tie wire at the mesial end to a hook or eyelet on a maxillary bicuspid and pushes at the distal end on a buccal tube or bracket attached to a maxillary molar. The compressed spring creates a force that tends to move the molars distally.

4 Claims, 3 Drawing Sheets

DISTALIZING SPRING

BACKGROUND OF THE INVENTION a. Field of the Invention

This invention relates to a dental appliance for distalizing molars in orthodontic treatment. In particular, this invention provides for a device in which three pieces, a coil spring, a head, and a ligature tie wire are attached in succession to provide a safe and easy means for moving maxillary molars.

b. Description of the Related Art

Orthodontic practice often requires a phase of treatment wherein it is necessary to move the maxillary molars. The distalization of maxillary molars is often accomplished with headgear or elastic bands. The headgear, which extends external to the patient's mouth is inserted and removed by the patient in accordance with a selected treatment schedule. Elastic bands are similarly inserted and removed by the patient. Use of headgear and elastics for molar distalization have several disadvantages.

Because headgear worn in conjunction with elastic bands are removable by the patient, a degree of patient compliance is required during the molar distalizing phase of treatment. Patient compliance is often an impediment to effective treatment. Some patients will refuse to wear the headgear necessary for distalizing molars, due to reasons of discomfort. Other patients may become dissatisfied with the appearance of the appliance. The problem with dissatisfaction with appearance may often be remedied where a patient is required to wear headgear only at night. But, discomfort while sleeping with the headgear in place may prevent a patient from wearing it while sleeping.

The effort necessary in being faithful to the repeated handling and the daily routine of placement and removal of any orthodontic appliance causes further obstacles to achieving the patient compliance necessary to complete molar distalizing treatment. It is also a burden on the patient to have to suffer the inconvenience of the cooperation necessary to achieve satisfactory results.

These problems with patient compliance can slow the progress of treatment. The headgear and elastics create a force to drive the molars distally. Each time the appliances are removed, the force is relieved, halting the movement of the molars. More importantly, removal of the appliance for prolonged periods results in reversal of treatment, as the progress previously made will be undone when the molars tend to return to their starting positions.

The use of headgear and elastic bands also introduces a potential safety problem. Because the parts are removable and require repeated handling, accidental swallowing of parts becomes possible. Also, it has been documented that headgear, when improperly used, may cause facial damage due to a slingshot effect.

SUMMARY

In view of the shortcomings of the prior art, it is an object of the present invention to provide for a device for moving molars in which a spring, a tubular coil head and a ligature tie wire are all attached.

It is a further object of the present invention to provide a molar distalizing device which minimizes the need for patient cooperation and thereby minimizes patient inconvenience.

It is a further object of the present invention to provide a distalizing device which is easily inserted into the mouth of a patient.

It is a further object of the present invention to provide a molar distalizing device which creates a constant force and thereby accelerates molar distalization treatment while reducing trauma and eliminating round tripping.

It is a further object of the present invention to provide a distalizing device in which the risk of swallowing of parts is minimized.

Briefly, the present invention is directed to a molar distalizing device which includes a spring with a first end and a second end, a tubular member attached to the first end of the spring, and means for attaching said tubular member to a bracket on a patient's tooth. This device may be used to distalize molars and thereby minimize or eliminate the need for headgear.

Other objective and advantages of the present invention will become apparent from the following description.

DETAILED DESCRIPTION OF THE INVENTION

Figure 1:
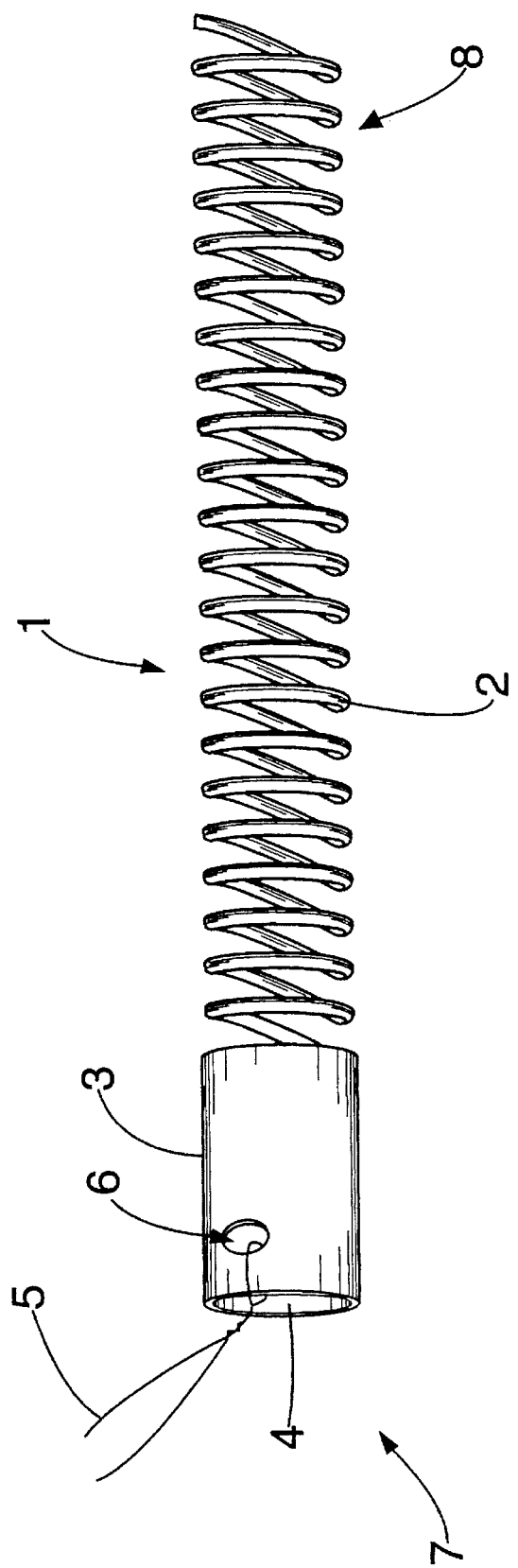
FIG. 1 shows the distalizing device of the present invention.

A distalizing device constructed in accordance with the present invention is illustrated in FIG. 1. The distalizing device 1 is generally elongated with mesial end 7 and distal end 8. The device 1 includes a coil spring 2. The coil spring 2 is preferably made from nickel titanium wire with superelastic properties. The spring may be stop wound or may be a continuous open coil with or without protection on the distal end of the coil. The spring inserts into a tubular head 3 with lumen 4. The spring 2 is fixed to the tubular head 3. In a preferred embodiment, the spring 2 and the tubular head 3 are attached by means of a ligature tie wire 5 fastening the spring 2 to the head 3 at hole 6 located in the wall of the head 3.

Figure 2:
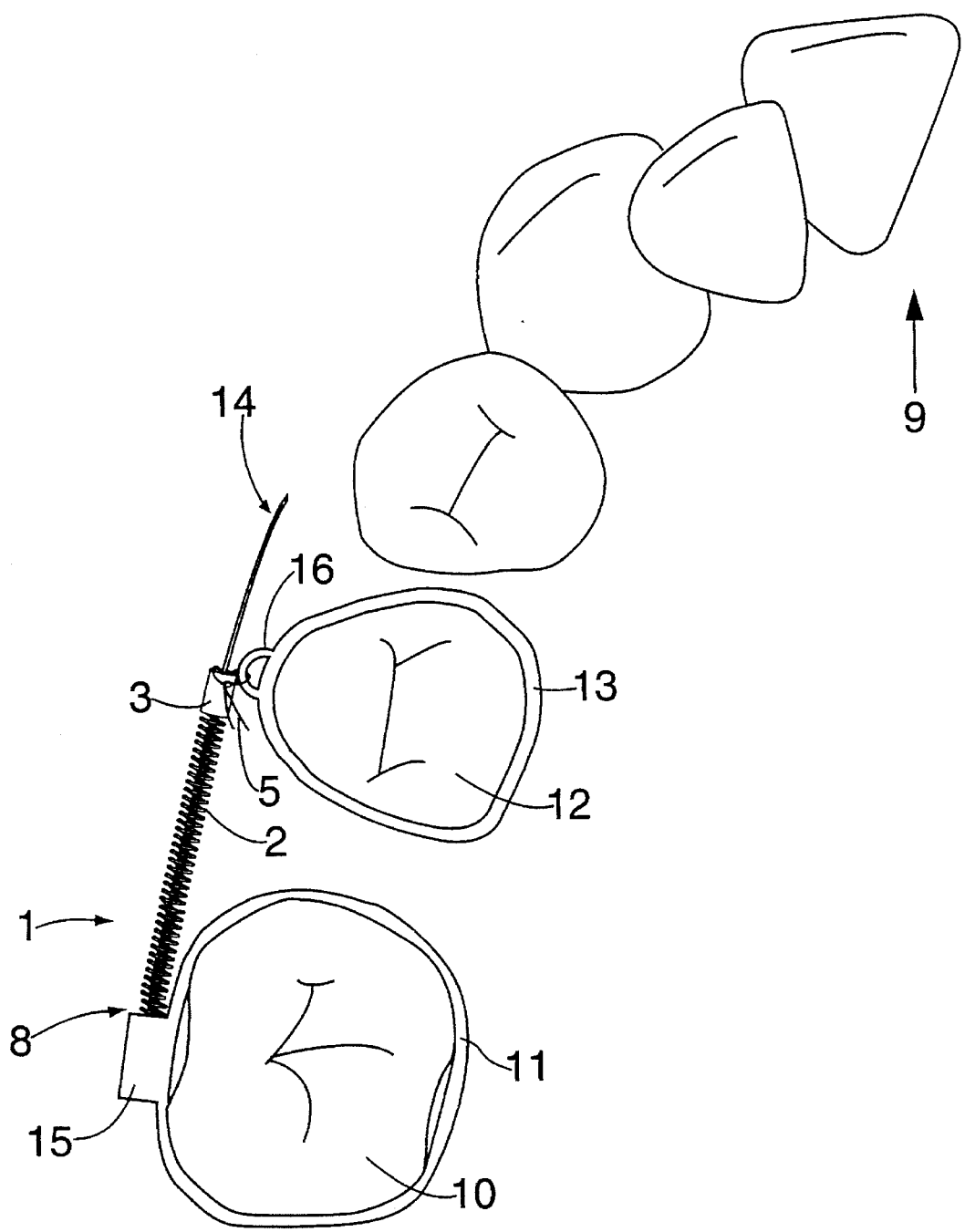
FIG. 2 shows the distalizing device of FIG. 1 in use inside the mouth of a patient.

FIG. 2 illustrates the distalizing device 1 in use inside a patient's mouth. The maxillary teeth are illustrated with the midline 9. Molar 10 with band 11 and buccal tube 15, and bicuspid 12 with band 13 are shown. An archwire 14 is threaded through the distalizing device 1, through the spring 2 and through the head 3. The distal end 8 of the distalizing device 1 is placed against a bracket or buccal tube 15 attached to the band 11 on molar tooth 10. The spring 2 is compressed and the ligature tie wire 5 is tied to a receiving device 16 on the bicuspid 12. The receiving device 16 is preferably an eyelet or hook to which the tie wire 5 may attach. The compressed spring 2, attached to the bicuspid 12 at mesial end 7, creates a force against buccal tube 15 which tends to move the molar 10 distally.

FIG. 2 illustrates the device 1 attached to a receiving device 16 on a second bicuspid. The scope of the present invention also covers use of the distalizing device attached to a first bicuspid. Use of the distalizing device with a first bicuspid may be preferable in some instances, and necessary where, for example, the second bicuspid has been extracted.

The molar distalizing device of the present invention is constructed such that all parts are attached and can be easily inserted into the mouth of a patient and cannot be removed by the patient. Thus, such a distalizing device, when made of a nickel titanium wire, provides a constant or continuous force on the maxillary molars.

Figure 3:
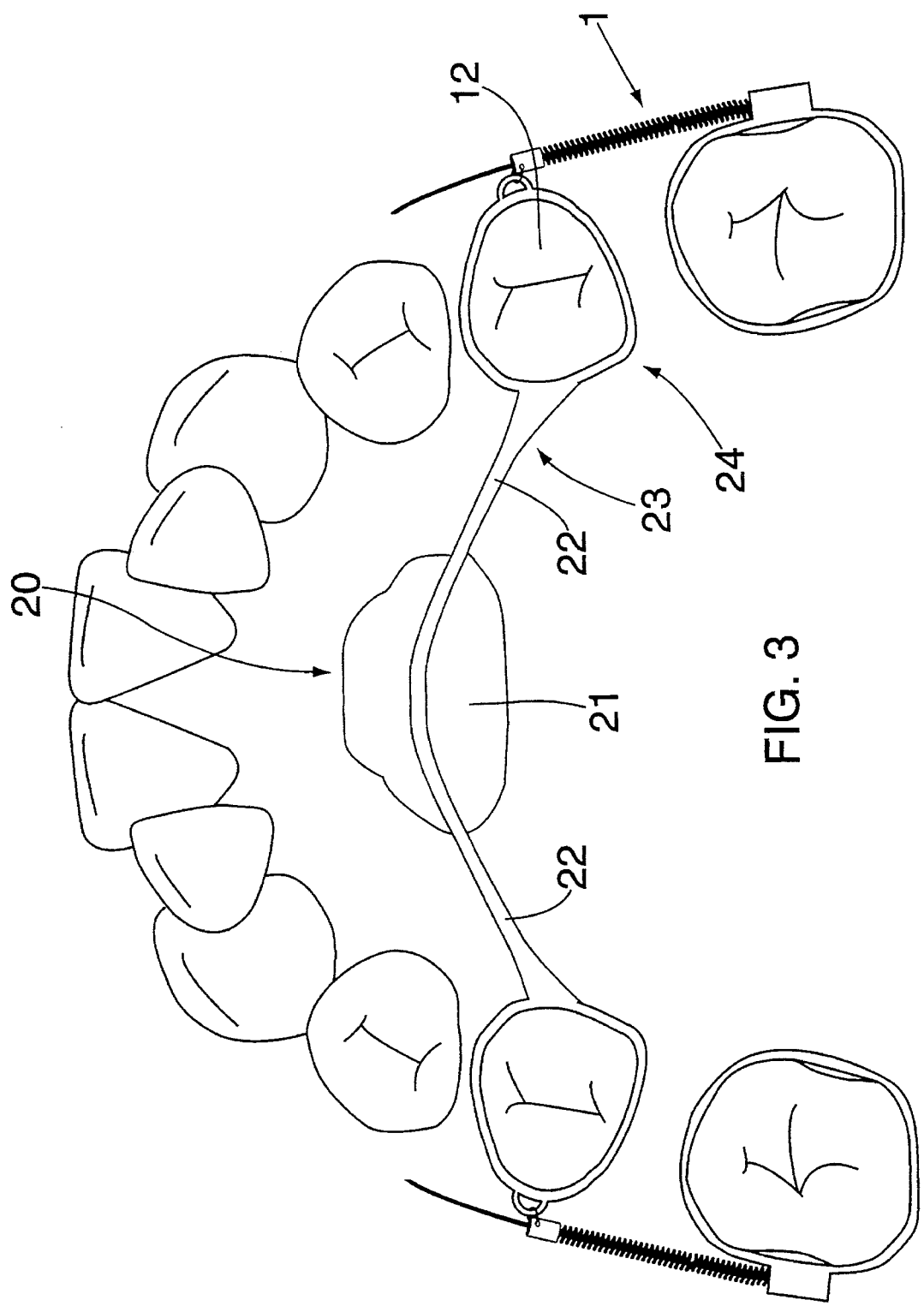
FIG. 3 shows the distalizing device of FIG. 1 used in conjunction with a retainer inside the mouth of a patient.

In another preferred embodiment, the distalizing device of the present invention may be used in conjunction with a retainer. FIG. 3 illustrates an embodiment of the present invention whereby the second bicuspid 12 is anchored to the anterior teeth by a retainer 20. A preferred retainer 20 includes an acrylic pad 21 resting on the anterior at the hard palate. Extending from the acrylic pad 21 are wires 22 soldered at distal ends 23 to the lingual surface of the bicuspid bands 24. The retainer 20 anchors the second bicuspids 12 to offset any reciprocal forces.

In the assembly illustrated in FIG. 3, the distalizing device 1 is attached to the teeth as in FIG. 2 above. Because the second bicuspid 12 is anchored to the hard plate by the retainer 20, movement of the maxillary molars 10 rather than the second bicuspids 12 is effected by the force created by the distalizing device 1.

FIG. 3 illustrates the device 1 attached to the second bicuspids 12, where the second bicuspids 12 are anchored by retainer 20. The scope of the present invention also covers use of the distalizing device in conjunction with a retainer anchoring the first bicuspids. In such a case, the distalizing device would also attach to the first bicuspids.

The distalizing device of the present invention has several advantages. It can be used either early or late in treatment. In a patient that will not wear headgear or elastics, the distalizing device offers a way to provide a continuous force to move the molars back without patient cooperation and with minimal inconvenience. It eliminates round tripping caused by intermittent force applications. Further, it eliminates the need, as described in U.S. Pat. No. 5,064,370, for auxiliary tubes and wires that are prone to failure and breakage while also causing patient discomfort.

Although the device may be a substitute for headgear, it may also be used to supplement the headgear. In cases where the distalizing device is used in conjunction with headgear, faster molar movement is accomplished. The distalizing device provides a constant force which arguments the force of the headgear during the daytime or at other times when the headgear is not in use. If a patient skips a day of headgear use, the distalizing device will still be providing a constant distal force, thus reducing any round tripping that may otherwise result due to the removal of the headgear. In this way the distalizing device of the present invention facilitates the continuity and advancement of treatment.

In the foregoing specification, the present invention has been described with respect to specific embodiments. These serve as examples to illustrate the invention rather than limit its scope. Modifications may be made without departing from the broader teachings and scope of the invention.

What is claimed is:

1. A molar distalizing system adaptable for use in conjunction with headgear, comprising:

a spring with a first end and a second end, a tubular member attached to the first end of the spring, means for attaching said tubular member to a receiving appliance on a patient's tooth, wherein the molar distalizing system in use causes movement of teeth under the force created by the spring being compressed.

2. A method of distalizing molars, comprising:

attaching a receiving means to a maxillary bicuspid in a patient's mouth;

attaching a stopping member to a maxillary molar in a patient's mouth;

attaching a spring means with mesial end and distal end at the mesial end to the receiving means on a maxillary bicuspid and fixing the distal end of said spring means at the stopping member on the maxillary molar such that said spring means pushes the stopping member distally;

wherein said spring means includes a tubular head with a mesial end and distal end including a lumen through its center and a hole in its wall near the mesial end; a coil with a mesial end and a distal end inserted into the lumen of the tubular head and connected at its mesial end to the mesial end of the tubular head; and a ligature tie wire threaded through the hole in said tubular head securing the mesial end of the coil inside and at the mesial end of the tubular head.

3. The method of distalizing molars of claim 2, wherein said coil is made from a nickel titanium wire.

4. The method of distalizing molars of claim 2, wherein said spring means is attached by threading an archwire from the bicuspid through the lumen of said tubular head and through said coil from its mesial to its distal end, fixing the distal end of said coil on said stopping member tube, compressing said coil, and securing said spring means with said coil in a compressed state by tying said ligature tie wire to said receiving means on the maxillary bicuspid such that a force is created which tends to move the maxillary molar distally.

\* \* \* \* \*

UNITED STATES PATENT AND TRADEMARK OFFICE
CERTIFICATE OF CORRECTION

PATENT NO. : 5,505,616
DATED      : April 9, 1996
INVENTOR(S): Anthony L. Harwell It is certified that error appears in the above-indentified patent and that said Letters Patent is hereby corrected as shown below:

```
Column 1, line 21, change "have" to --has--.

Column 2, line 19, change "objective" to --objectives--.

Column 3, line 44, change "arguments" to --augments--.

Column 4, line 44, delete "tube" at end of line.
```

Signed and Sealed this

Twenty-seventh Day of August, 1996

Attest:

BRUCE LEHMAN

*Attesting Officer*     *Commissioner of Patents and Trademarks*